United States Patent
Cao et al.

(10) Patent No.: US 12,145,969 B2
(45) Date of Patent: Nov. 19, 2024

(54) COMPOSITIONS AND METHODS RELATING TO NOVEL SULFONO-GAMMA-AA PEPTIDES

(71) Applicant: University of South Florida, Tampa, FL (US)

(72) Inventors: Chuanhai Cao, Tampa, FL (US); Jianfeng Cai, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 141 days.

(21) Appl. No.: 17/575,080

(22) Filed: Jan. 13, 2022

(65) Prior Publication Data

US 2022/0220167 A1     Jul. 14, 2022

Related U.S. Application Data

(60) Provisional application No. 63/136,903, filed on Jan. 13, 2021.

(51) Int. Cl.
| | |
|---|---|
| *C07K 14/47* | (2006.01) |
| *A61P 25/00* | (2006.01) |
| *A61K 38/00* | (2006.01) |

(52) U.S. Cl.
CPC .............. *C07K 14/47* (2013.01); *A61P 25/00* (2018.01); *A61K 38/00* (2013.01)

(58) Field of Classification Search
None
See application file for complete search history.

(56) References Cited

U.S. PATENT DOCUMENTS

| | | |
|---|---|---|
| 7,528,112 B2 | 5/2009 | Cunningham et al. |
| 9,585,932 B2 | 3/2017 | Lu et al. |

FOREIGN PATENT DOCUMENTS

| | | |
|---|---|---|
| WO | 2017147044 A1 | 8/2017 |
| WO | 2019136310 A2 | 7/2019 |

OTHER PUBLICATIONS

She et al., De Novo Left-Handed Synthetic Peptidomimetic Foldamers. Angewandte Chemie International Edition, 2018, 57, 9916-9920.*

Nimmagadda et al., γ-AApepetides as a new strategy for therapeutic development. Current Medicinal Chemistry, 2019, 26, 2313-2329.*

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Chen, R. P. Y. "From nose to brain: The promise of peptide therapy for Alzheimer's disease and other neurodegenerative diseases." J. Alzheimers Dis. Parkinsonism 7.314 (2017): 2161-0460.

* cited by examiner

*Primary Examiner* — Po-Chih Chen
(74) *Attorney, Agent, or Firm* — Quarles & Brady LLP

(57) ABSTRACT

Provided herein are compounds, compositions, pharmaceutical compositions, kits, and methods relating to novel sulfono-γ-AA peptides. Novel sulfono-γ-AA peptides as described herein can have the structure according to Formula 1:

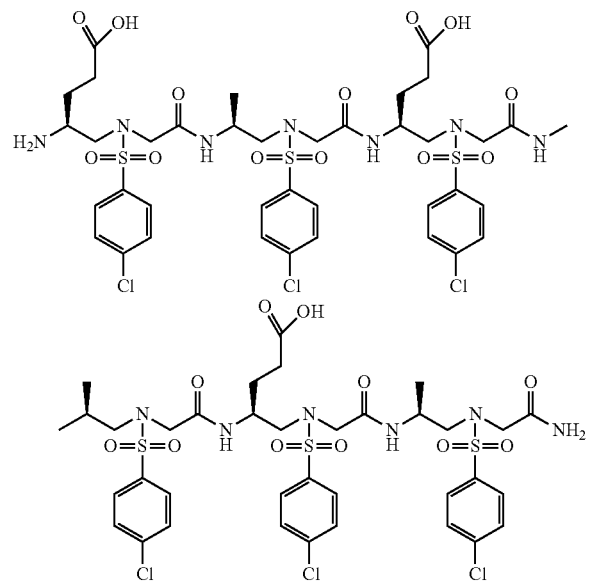

In embodiments according to the present disclosure, novel sulfono-γ-AA peptides as described herein have minimal toxicity, can repair neuronal damage, inhibit Amyloid beta aggregation, and promote cellular growth and viability.

17 Claims, 17 Drawing Sheets

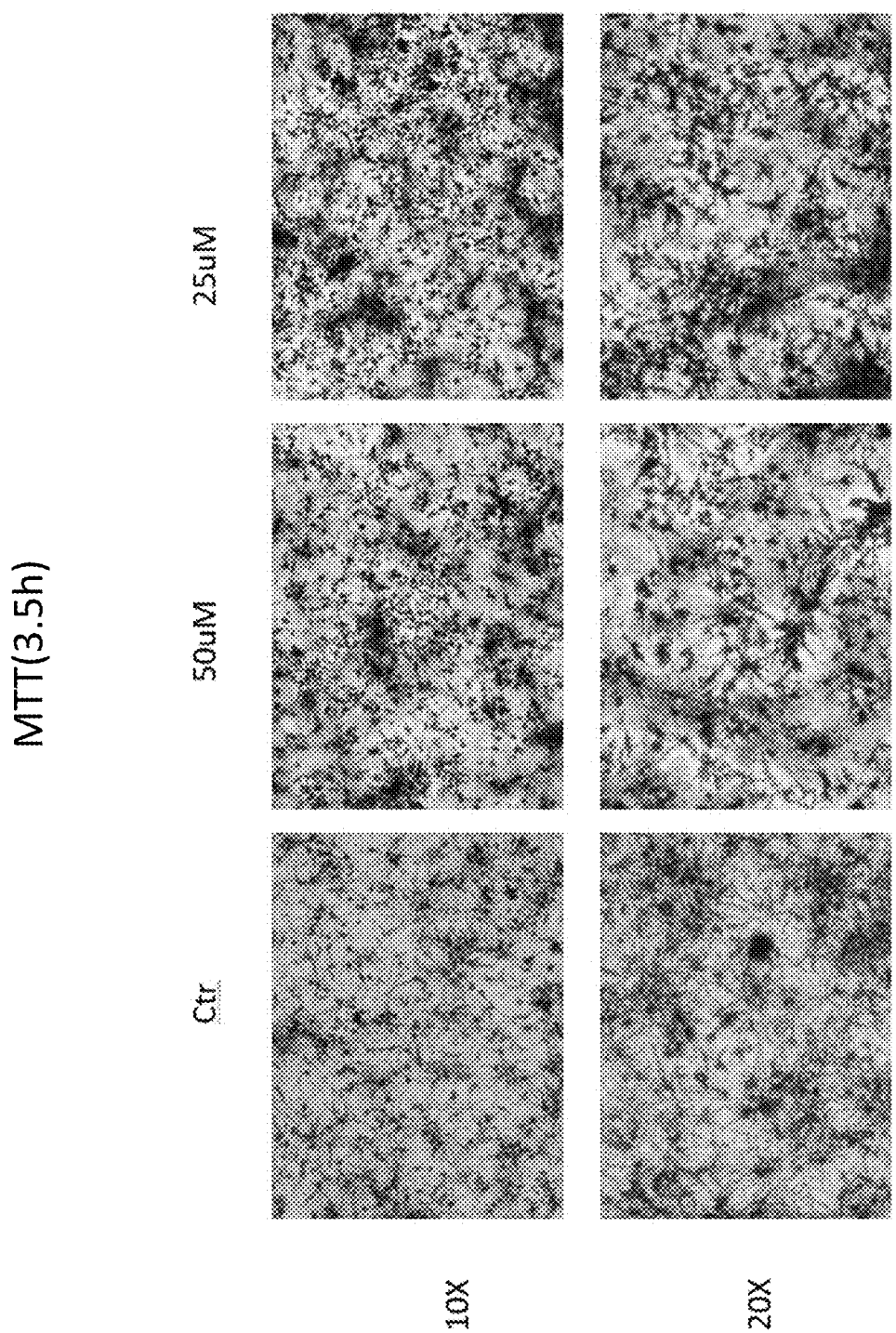

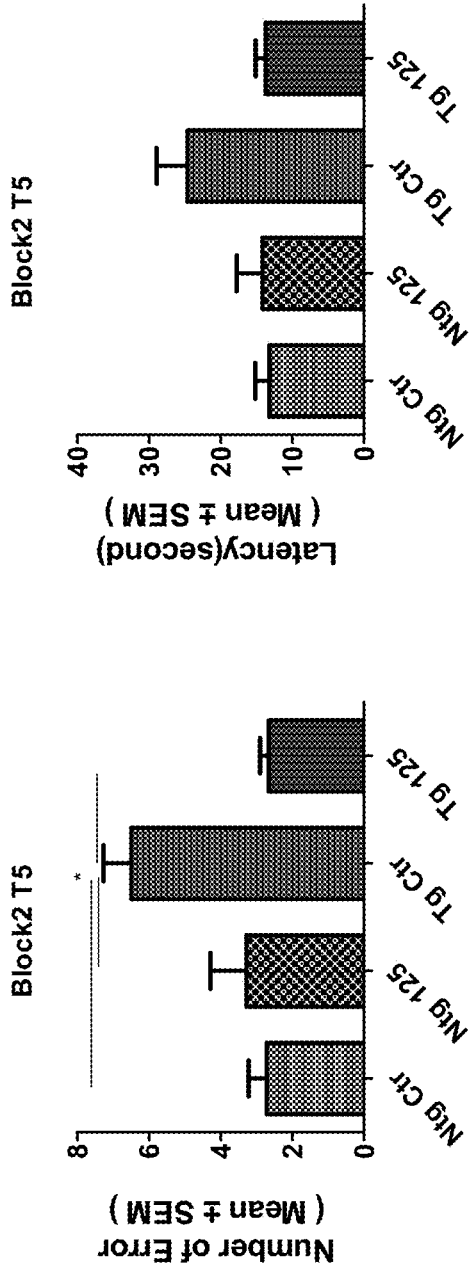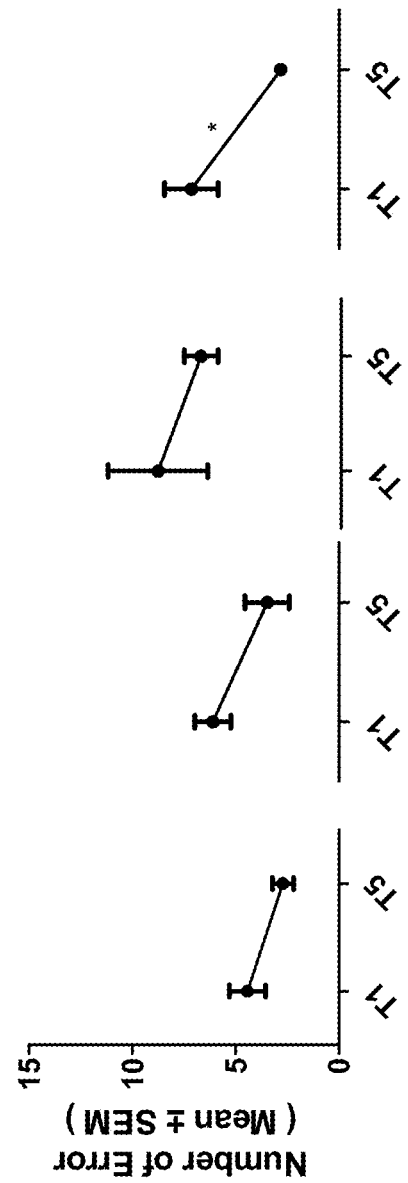
FIG. 12A
FIG. 12B
FIG. 12C

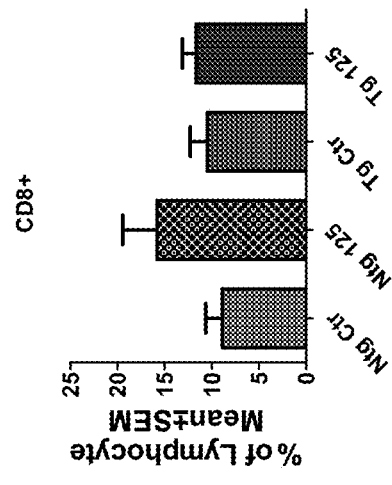
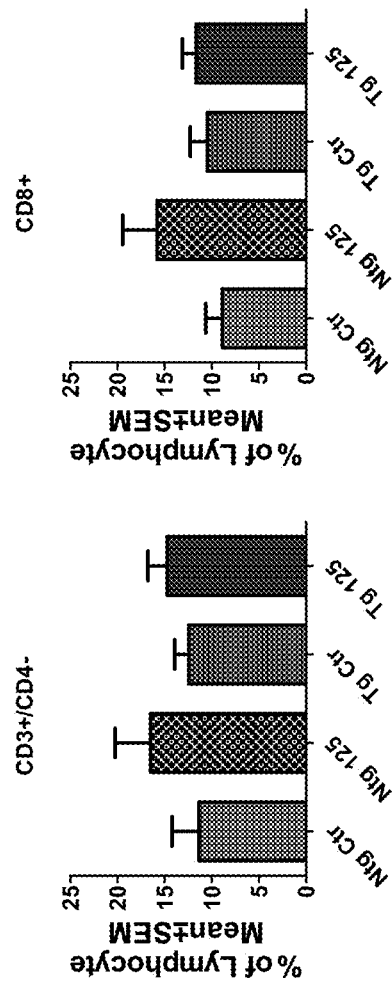
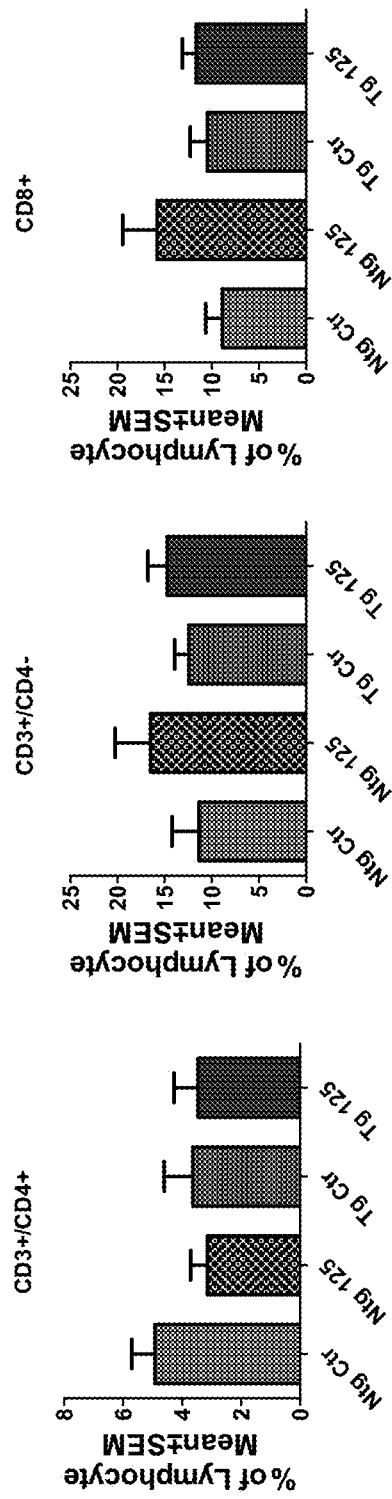
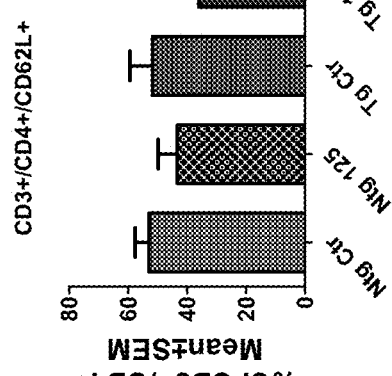
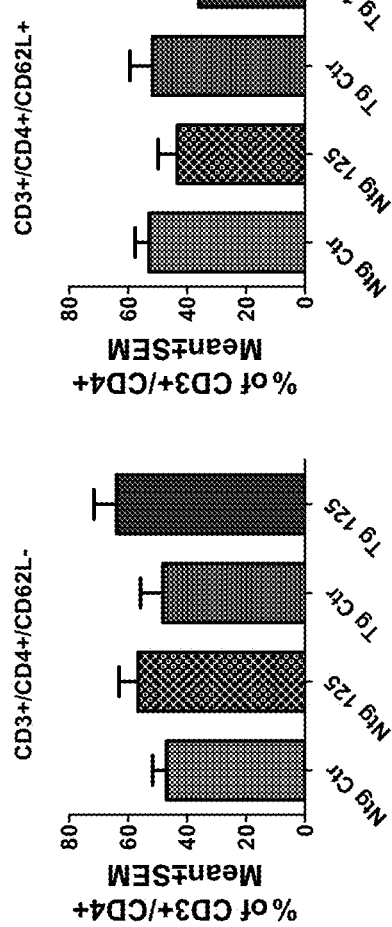

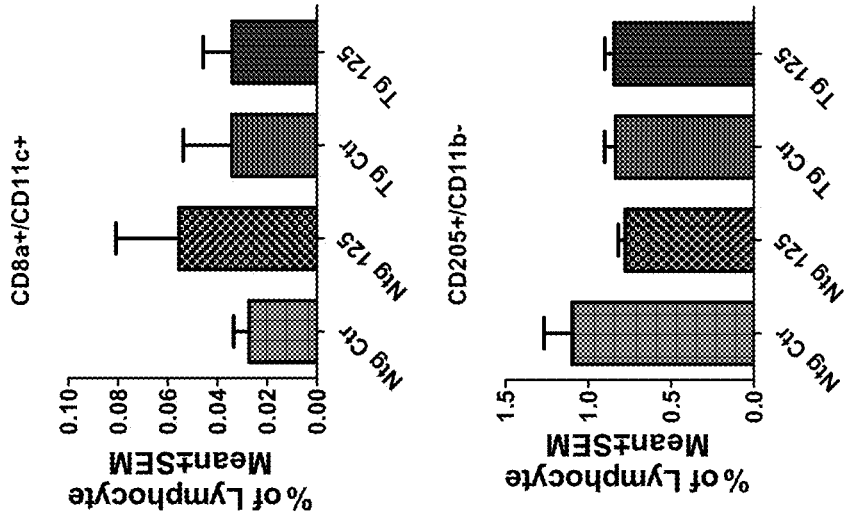
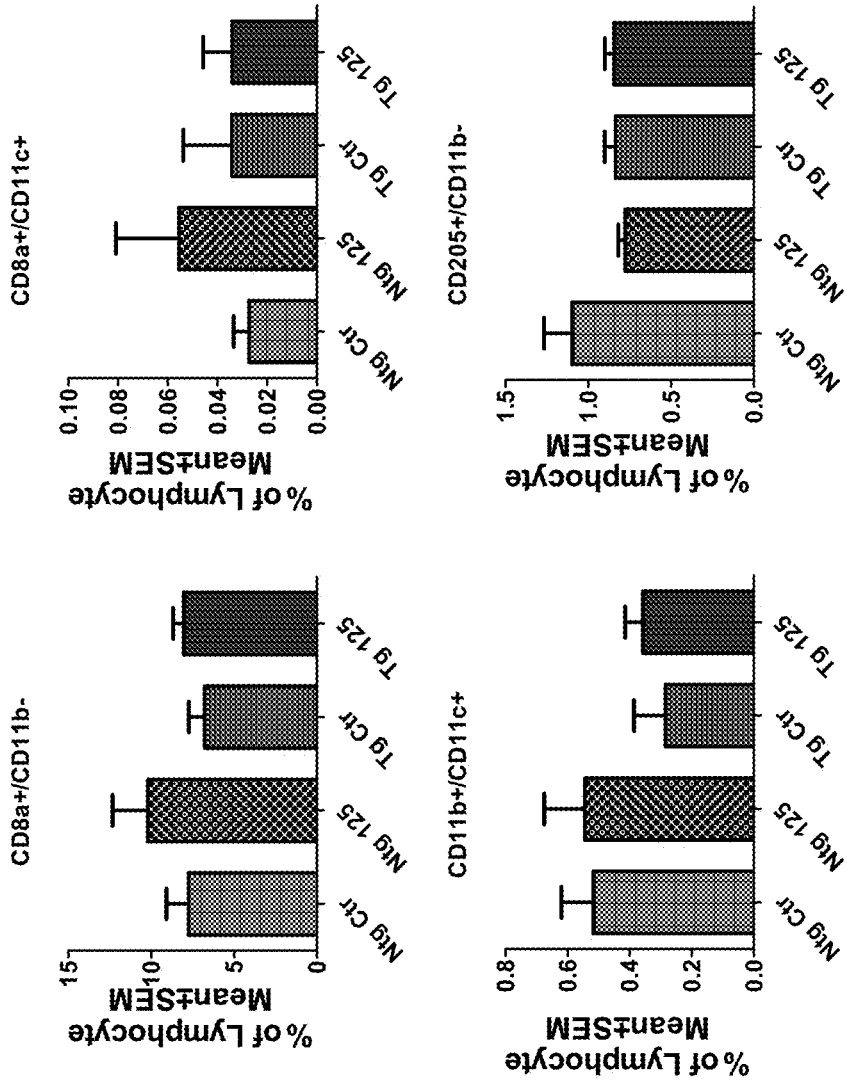

Formula 1

COMPOSITIONS AND METHODS RELATING TO NOVEL SULFONO-GAMMA-AA PEPTIDES

CROSS-REFERENCE TO RELATED APPLICATIONS

This application claims priority to U.S. Provisional Application No. 63/136,903 filed on Jan. 13, 2021, the contents of which are incorporated by reference in its entirety.

BACKGROUND

Effective therapies and/or cures for central nervous system (CNS) disorders, which impose a tremendous socioeconomic burden, are currently lacking. In particular, there is currently no effective drug for Alzheimer's disease. Currently, all inhibitors for gamma and beta secretase are all failed when tested on human. Also, immunotherapy (both active and passive) are under difficulties to move into clinical use due to either efficacy or safety issue. There is a desperate need for AD prevention or treatment. As such, there exists a need for improved pharmaceuticals for treating and preventing these diseases or symptoms thereof.

SUMMARY

Described herein and compositions and methods relating to sulfono-γ-AA peptides. Described herein is a sulfono-γ-AA peptide according to Formula 1 and having the structure:

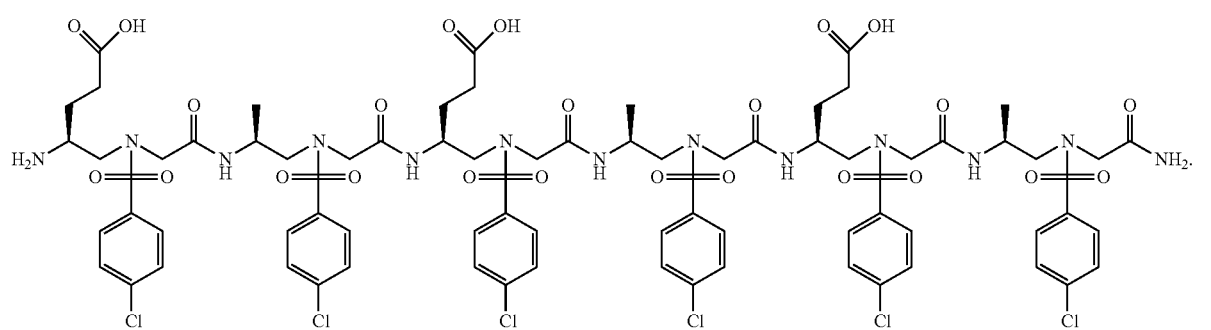

Formula 1

Described herein is a pharmaceutical formulation comprising a sulfono-γ-AA peptide according to Formula 1 and having the structure:

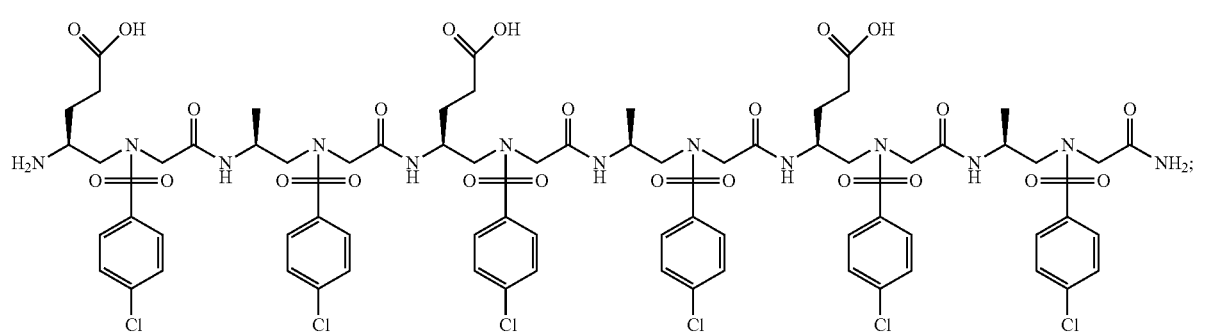

Formula 1 and a pharmaceutically-acceptable carrier.

In embodiments, the pharmaceutical formulation comprises an effective amount of sulfono-γ-AA peptide. In embodiments, the effective amount of sulfono-γ-AA peptide is an amount effective to improve working memory according to a working memory assay suitable for the subject in need thereof. In embodiments, the effective amount of sulfono-γ-AA peptide is a concentration about 1 mg to 200 mg per day.

Described herein are methods of treating a disease or disorder of the central nervous system in a subject in need thereof, or a symptom thereof. In an embodiment, the method comprises administering a pharmaceutical formulation comprising a sulfono-γ-AA peptide to the subject in need thereof, wherein the sulfono-γ-AA peptide is a compound of Formula 1 and having the structure:

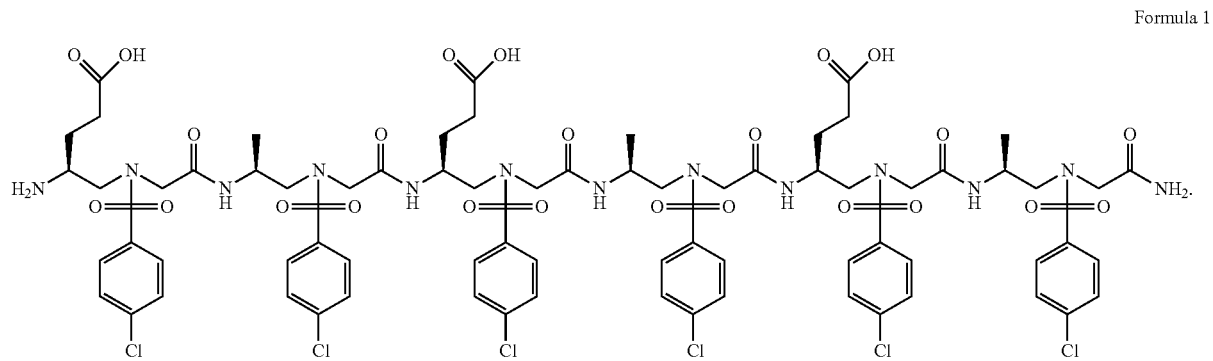

Formula 1

In embodiments, the pharmaceutical formulation further comprises a pharmaceutically acceptable carrier. In embodiments, the pharmaceutical formulation comprises an effective amount of sulfono-γ-AA peptide. In embodiments, the effective amount of sulfono-γ-AA peptide is a concentration of about 1 mg to 200 mg per day. In embodiments, the effective amount of sulfono-γ-AA peptide is an amount to improve working memory in the subject in need thereof. In embodiments, the subject in need thereof has a disorder of the central nervous system. In embodiments, the subject in need thereof has a neurodegenerative disease or a symptom thereof. In embodiments, the subject in need thereof has or is suspected of having for Alzheimer's disease, Lewy body dementia, dementia, Parkinson's disease, Huntington's disease, amyotrophic lateral sclerosis (ALS), other acute or chronic neuronal damage, spinal cord damage, and trauma brain injury, or symptoms thereof. In embodiments, the subject in need thereof is a subject having or suspected of having Alzheimer's disease. In embodiments, the subject in need thereof is a subject having or suspected of having symptoms of Alzheimer's disease. In embodiments, the subject in need thereof performs worse in working memory tests compared to an otherwise healthy control subject as assessed by a suitable working memory assay.

Described herein are methods of improving cellular viability in a population of cells. In an embodiment, methods can comprise administering a pharmaceutical formulation comprising a sulfono-γ-AA peptide to population of cells, wherein the sulfono-γ-AA peptide is a compound of Formula 1 and having the structure:

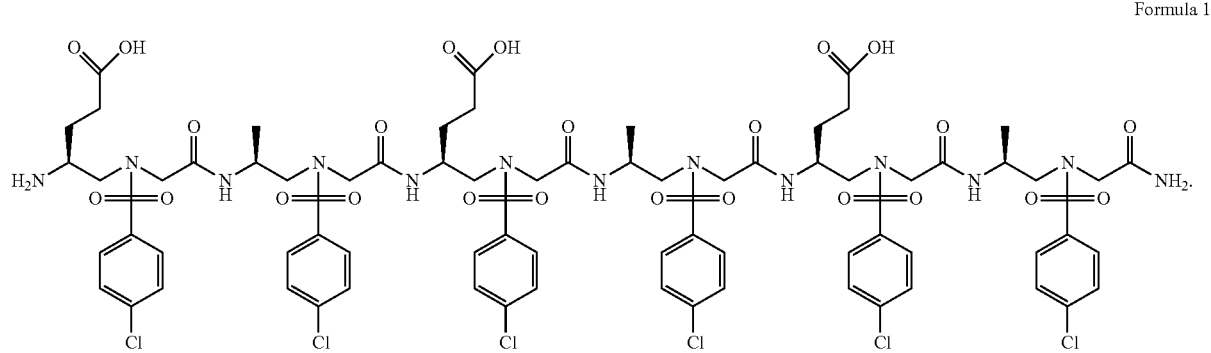

Formula 1

In embodiments, the pharmaceutical formulation further comprises a pharmaceutically acceptable carrier. In embodiments, the pharmaceutical formulation comprises an effective amount of sulfono-γ-AA peptide. In embodiments, the effective amount of sulfono-γ-AA peptide is a concentration of about 1 mg to 200 mg per day. In embodiments, the effective amount of sulfono-γ-AA peptide is an amount to improve cellular viability according to a MTT assay. In embodiments, the population of cells is a population of spleen cells or neuronal cells. In embodiments, the population of cells is from or resides in a subject having a disorder of the central nervous system or symptoms thereof. In embodiments, the population of cells comprises glial cells. In embodiments, the population of cells is from or resides in a subject having a neurodegenerative disease or symptom thereof. In embodiments, the population of cells is from or resides in a subject having Alzheimer's disease, Lewy body dementia, dementia, Parkinson's disease, Huntington's disease, amyotrophic lateral sclerosis (ALS), other acute or chronic neuronal damage, spinal cord damage, and trauma brain injury, or symptoms thereof. In embodiments, the population of cells is from or resides in a subject who performs worse in working memory tests compared to an otherwise healthy control subject as assessed by a suitable working memory assay.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 7A-7C are bright field micrographs showing murine primary neurons exposed to sulfono-γ-AA peptide FS-125-6-b 3.5 hours into MTT treatment. Control cells with vehicle are shown at 10× and 20× (FIG. 7A), whereas cells exposed to sulfono-γ-AA peptide FS-125-6-b are shown at 10× and 20× in FIGS. 7B and 7C (50 μM and 25 μM, respectively).

FIGS. 12A-12C are plots showing Block2 number of errors (FIGS. 12A, 12C) and latency (FIG. 12B) in animals following two months of treatment with FS-125-6-b.

FIGS. 14A-14E are plots of flow cytometry results for CD3+/CD4+, CD3/CD−, and CD8+ lymphocytes (expressed as a percentage of total lymphocytes, mean+SEM; FIGS. 14A-14C, respectively) and CD+/CD4+/CD62L− and CD+/CD4+/CD62L+ (expressed as a percentage of total CD3+/CD4+; FIGS. 14D-14E, respectively) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).

FIGS. 16A-16D are plots of flow cytometry results for CD8a+/CD11b−, CD8a+/CD11c+, CD11b+/CD11c+, and CD205+/CD11b− lymphocytes (expressed as a percentage of total lymphocytes, mean+SEM; FIGS. 16A-16D, respectively) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).

DETAILED DESCRIPTION

Figure 1A:
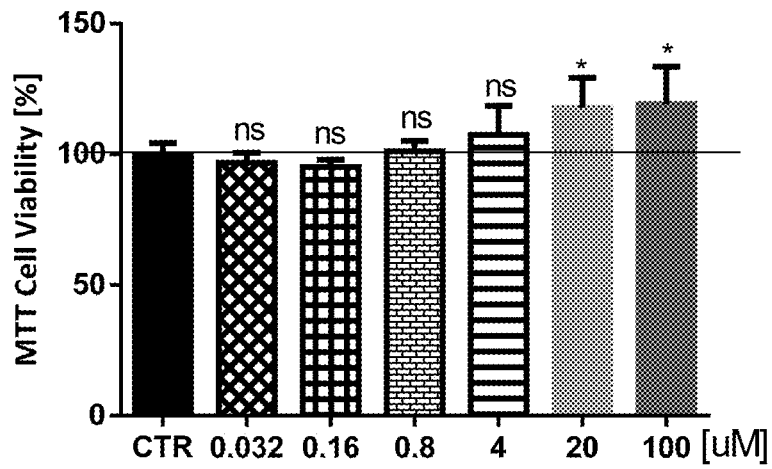
FIGS. 1A-1B are graphs showing cell viability results of a stable mouse N2a/APP cell line (transfected to stably express human amyloid precursor protein, APP) exposed to sulfono-γ-AA peptide FS-125-6-b as determined by 3-(4,5-dimethylthiazol-2-yl)-2,5-diphenyltetrazolium bromide (MTT) assay.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, chemistry, organic chemistry, biochemistry, pharmacology, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "administering" can refer to any administration route, including but not limited to administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, inter nasal, intrathecal, intrahepatic, intralesional, and intracranial injections or infusion techniques.

As used interchangeably herein, "biocompatible," "biocompatibility," and "biologically compatible" refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "cancer" can refer to any disease within the collection of related diseases whose etiology and/or pathology involve abnormal cell growth and proliferation that can include invasion into surrounding and/or distant tissues. Cancerous tumors can be malignant or benign.

As used herein, "chemotherapeutic" refers to a chemical compound or agent used to treat, control, or cure a disease or symptoms thereof, particularly cancer.

As used herein, "composition" or "formulation" can refer to a combination of an active agent(s) and another compound or composition, inert (for example, a detectable agent or label) or active, such as an adjuvant.

As used herein, "a compound of formula (1), (2), (3), (4), (5), (6), (7), (8), (9), (10), (11), (12), (13), (14), and so forth and so on," or "a compound having a structure according to formula (1), (2), (3), (4), (5), (6), (7), (8), (9), (10), (11), (12), (13), (14), and so forth and so on" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" when used in reference to an amount of a molecule, compound, or composition including but not limited to, a chemical compound, polynucleotide, peptide, polypeptide, protein, antibody, or fragments thereof, can indicate that the sample is distinguishable from its naturally occurring counterpart in that the concentration or number of molecules per volume is less than that of its naturally occurring counterpart.

As used herein, "effective amount" is an amount sufficient to effect beneficial or desired results. An effective amount can be administered in one or more administrations, applications, or dosages. "Effective amount" can refer to an amount of a sulfono-γ-AA peptide provided herein (e.g. a compound according to Formula 1 or a structural analogue thereof) that can improve working memory or cellular viability, which can be measured using a suitable assay (including, but not limited to, a MTT assay or memory test). Structural analogues of a sulfono-γ-AA peptide provided herein are those structural analogues that carry the same backbone but can be substituted in one or more position. "Effective amount" can refer to an amount of a sulfono-γ-AA peptide provided herein that can improve working memory and/or cellular viability in a subject having a nervous system disorder or symptoms thereof. "Effective amount" can refer to an amount of a sulfono-γ-AA peptide that can treat or prevent a nervous system disorder or symptom thereof in a subject. "Effective amount" can refer to an amount of a sulfono-γ-AA peptide that can treat or prevent neurodegenerative diseases or a symptom thereof. "Effective amount" can refer to an amount of a sulfono-γ-AA peptide that can treat or prevent or delay onset or symptoms of Alzheimer's disease, Parkinson's, Huntington, ALS disease, other neuronal damage, spinal cord damage, and trauma brain injury in a subject having or suspected of having such. The "effective amount" can also refer to the least amount sufficient to effect beneficial or desired results, which are discussed above.

As used herein, "hydrate" refers to a compound formed by the addition of water. Typically, but not always, this will be crystalline lattice structures that incorporate water molecules. Hydrates include stoichiometric hydrates, as well as compositions containing variable amounts of water.

As used herein, "metabolic syndrome" can refer to a group of metabolic risk factors such as hyperglycemia, hypertension, insulin resistance, and cholesterol abnormalities, which increase the risk for cardiovascular diseases and type 2 diabetes.

As used herein, "mitigate" can refer to reducing a particular characteristic, symptom, or other biological or physiological parameter associated with a disease or disorder.

As used herein, "obese" can refer to the condition of a subject where a subject has a Body mass index (BMI) of greater than about 30. BMI is calculated as the individual's weight on kilograms divided by height in meters squared.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount" can refer to an amount of a compound or formulation thereof provided herein that can prevent diabetes, cancer, an inflammatory disease (such as osteoarthritis), obesity, insulin resistance, metabolic syndrome hepatosteatosis, a cardiovascular disease, neurodegenerative diseases or a symptom thereof. In embodiments, the "pharmaceutically effective amount" can be the least amount of a compound or formulation thereof provided herein needed to treat, prevent, or elicit the desired biological and/or medical effect in the response of a cell, tissue, organ, system, or subject that is being sought by the researcher, veterinarian, medical doctor or other clinician as described above. In some embodiments, the "pharmaceutically effective amount" can be the least amount that can treat or prevent diabetes, cancer, an inflammatory disease (such as osteoarthritis), obesity, insulin resistance, metabolic syndrome hepatosteatosis, a cardiovascular disease, neurodegenerative diseases or a symptom thereof. "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician as discussed above. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" refers to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "preventative," "preventing," "prevent" and the like refer to partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to prevent diabetes, cancer, an inflammatory disease (such as osteoarthritis), obesity, insulin resistance, metabolic syndrome hepatosteatosis, a cardiovascular disease, a neurodegenerative diseases or a symptom thereof.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. Formula 1 or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat" and the like can refer to include partially or completely delaying, alleviating, mitigating or reducing the intensity of one or more attendant symptoms of a disease or condition including, but not limited to, diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

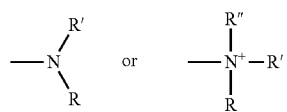

wherein R, R', and R" each independently represent a hydrogen, an alkyl, an alkenyl, —$(CH2)_m$-$R_C$ or R and R' taken together with the N atom to which they are attached complete a heterocycle having from 4 to 8 atoms in the ring structure; $R_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloalkly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

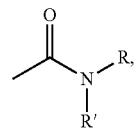

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by –O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

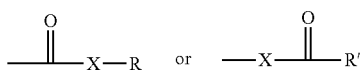

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; and the term "hydroxyl" refers to —OH.

As used herein, the term "sulfonyl" refers either to a functional group found primarily in sulfones or to a substituent obtained from a sulfonic acid by the removal of the hydroxyl group similarly to acyl groups. Sulfonyl groups have the general formula R—S(=O)2-R', where there are two double bonds between the sulfur and oxygen.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

As used herein, "about" indicates ±5% of the reference value, in an embodiment. In another embodiment, "about" indicates ±10% of the reference value. In another embodiment, "about" indicates ±1% of the reference value.

Discussion

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Described herein are sulfono-γ-AA peptides. In embodiments, further described herein are compositions comprising, kits comprising, and methods of using such. In embodiments according to the present disclosure, sulfono-γ-AA peptides as described herein can be utilized in methods according to the present disclosure as a potential treatment for neurological disease and a method to promote neuron generation.

A new class of peptidomimetics sulfono-γ-AA peptides.125, 126 has recently been developed. These new sulfono-γ-AA peptides take advantage of immense chemical diversity with various sulfonyl side chains, along with remarkable resistance toward proteolytic degradation. The peptides have been tested for anti-amyloid aggregation activity and neuronal toxicity. It is shown that some peptide has anti-Amyloid beta aggregation activity and also has ability of promoting neuron growth in vitro. In vivo data further demonstrates that the compound 126-6B can slow down memory declining, at least in animal models of Alzheimer's (for example in APP/PS1 mouse model).

There is no effective drug for Alzheimer's disease. Currently, all inhibitors for gamma and beta secretase are all failed when tested on human. Also, immunotherapy (both active and passive) are under difficulties to move into clinical use due to either efficacy or safety issue. There is a desperate need for AD prevention or treatment. This novel sulfono-γ-AA peptides has very minimal toxicity and not only inhibit Amyloid beta aggregation, but also promote neuron growth. It may also be used for repairing neuronal damage.

A novel peptide mimics has been designed and tested them on fighting Alzheimer's disease. Results demonstrate a peptide named 125-6b can inhibit Amyloid beta aggregation and also can promote neuron growth. It can also prevent memory impairment on APP/PS1 mouse model. These effects are not limited to Alzheimer's disease, however, and the peptide can be used for any neurological disease treatment and able to fix neuronal damage.

Sulfono-γ-AA Peptides

Sulfono-γ-AApeptides are a sub-class of γ-AApeptides that are oligomers of N-acylated-N-aminoethyl amino acids with enormous potential in functional group diversity. Like γ-AApeptides, sulfono-γ-AApeptides are able to display the same number of side chains as conventional peptides of equal length, endowing them with the ability to mimic bioactive peptides.

Figure 17:
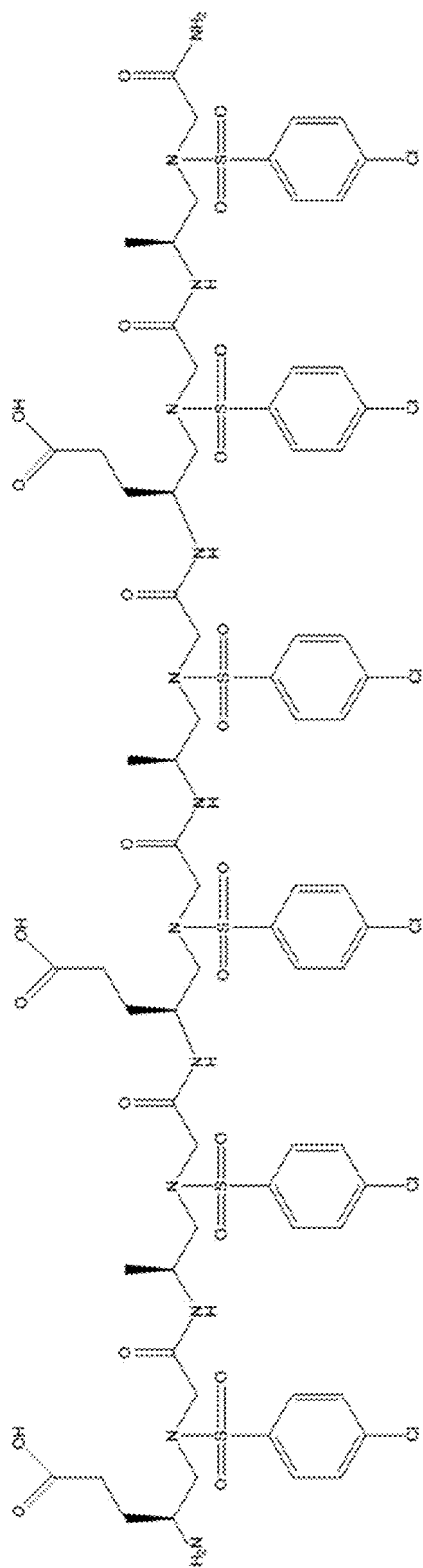
FIG. 17 shows the chemical structure (Formula 1) of compound FS-B-126-6-b.

Described herein are novel sulfono-γ-AA peptides. Sulfono-γ-AA peptides as described herein can have the chemical formula $C_{72}H_{87}Cl_6N_{13}O_{24}S_6$ (mass 1919.2442, molecular weight 1923.6150) and structure according Formula 1 (FIG. 17):

Formula 1

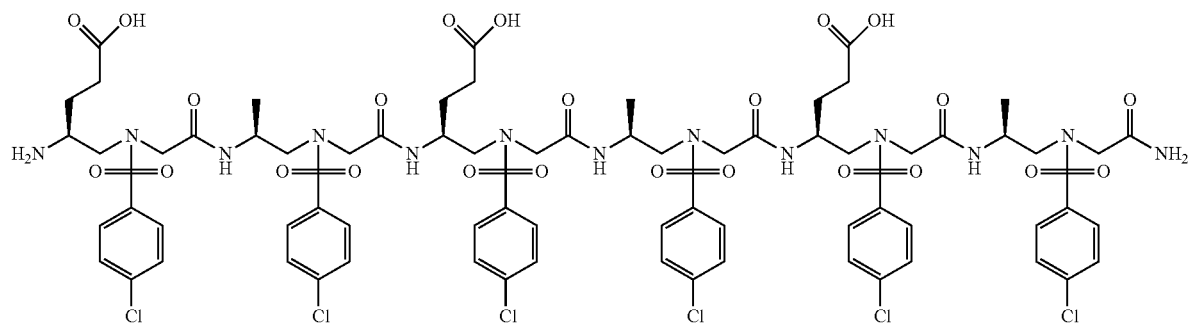

(mass 1919.2442, molecular weight 1923.6150)

Pharmaceutical Formulations of Sulfono-γ-AA Peptides

Provided herein are pharmaceutical formulations that can contain an amount of a compound having a structure of Formula 1 above (or a structural analogue thereof) and a pharmaceutically acceptable carrier.

Also provided herein are pharmaceutical formulations that can include and amount, such as an effective amount, least effective amount, and/or a pharmaceutically effective amount of a sulfono-γ-AA peptide. In some aspects that pharmaceutical formulation can include one or more of any one of compounds having a structure according to Formula 1 or a structural analogue thereof. In some aspects, a sulfono-γ-AA peptide can have a structure according to Formula 1. In some aspects, a sulfono-γ-AA peptide can have a structure according to Formula 1 or a structural analogue thereof.

The compounds described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

Pharmaceutically Acceptable Carriers and Auxiliary Ingredients and Agents

The pharmaceutical formulations containing an amount, such as an effective amount, least effective amount, and/or pharmaceutically effective amount of a compound described herein, or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective Amounts of the Sulfono-γ-AA Peptide and Auxiliary Active Agents

In some aspects, the effective amount, least effective amount, and/or pharmaceutically effective amount of the sulfono-γ-AA peptide having a Formula according to Formula 1 or a structural analogue thereof can improve working memory and/or cellular viability in a subject in need thereof or a population of cells. In some aspects, the effective amount, least effective amount, and/or pharmaceutically effective amount of the sulfono-γ-AA peptide that can have a Formula according to Formula 1 can inhibit can improve working memory and/or cellular viability in a subject in need thereof or a population of cells. In some aspects, the effective amount, least effective amount, and/or pharmaceutically effective amount of the sulfono-γ-AA peptide that can have a Formula according to Formula 1 can inhibit can improve working memory and/or cellular viability in a subject having or suspected of having a neurodegenerative disorder, for example Alzheimer's disease, Parkinson's disease, Huntington's disease, amyotrophic lateral sclerosis (ALS), other acute or chronic neuronal damage, spinal cord damage, and trauma brain injury. The effective amount, least effective amount, and/or pharmaceutically effective amount of the sulfono-γ-AA peptide that can have a structure according to Formula 1 or a structural analogue thereof contained in the pharmaceutical formulation can range from about 0.001 micrograms to about 1000 grams, about 0.01 micrograms to about 100 grams, about 0.1 micrograms to about 10 grams, or about 1 microgram to about 1 gram, about 10 micrograms to about 100 mg, 100 micrograms to about 10 mg, or about 1 mg to about 5 mg. In some embodiments, the effective concentration can range from about 1 pM to about 100 nM, about 10 μM to about 10 nM, or about 100 pm, to about 1 nM.

In certain aspects, the effective amount can be a concentration of about 5 mM. In certain aspects, the effective amount can be a concentration of about 0.1 μM to about 50 μM or about 0.1 to about 200 μM. In certain aspects, the effective amount can be about 1 mg to about 200 mg per day.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

In certain aspects, the effective amount can be a concentration of about 5 mM. In certain aspects, the effective amount can be a concentration of about 0.1 μM to about 50 μM or about 0.1 to about 200 μM.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage forms can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art. In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution.

The oral dosage form can be administered to a subject in need thereof. The oral dosage form can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

Where appropriate, the dosage forms described herein can be microencapsulated. The dosage form can also be prepared to prolong or sustain the release of any ingredient. In some embodiments, a compound of Formula 1 or a structural analogue thereof, a sulfono-γ-AA peptide according to Formula 1 or a structural analogue thereof, a sulfono-γ-AA peptide according to Formula 1, auxiliary active ingredient, and/or pharmaceutically acceptable salt thereof can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound of Formula 1 or a structural analogue thereof, a sulfono-γ-AA peptide according to any one of Formula 1 or a structural analogue thereof, a sulfono-γ-AA peptide according to Formula 1, auxiliary active ingredient, and/or pharmaceutically acceptable salt thereof can be integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation.

The liposomal formulation can be administered to a subject in need thereof. The liposomal formulation can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a compound of Formula 1 or a structural analogue thereof, a sulfono-γ-AA peptide according to Formula 1 or a structural analogue thereof, a sulfono-γ-AA peptide according to Formula 1 or a structural analogue thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

The nasal/inhalation formulations can be administered to a subject in need thereof. The nasal/inhalation formulations can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art. In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

In some embodiments, the dosage forms are aerosol formulations suitable for administration by inhalation. In some of these embodiments, the aerosol formulation contains a solution or fine suspension of a compound of Formula 1 or a structural analogue thereof, a sulfono-γ-AA peptide according to Formula 1 or a structural analogue thereof, a sulfono-γ-AA peptide according to Formula 1 or a structural analogue thereof, auxiliary active ingredient, and/or pharmaceutically acceptable salt thereof and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

The aerosol formulations can be administered to a subject in need thereof. The aerosol formulations can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

For some dosage forms suitable and/or adapted for inhaled administration, the pharmaceutical formulation is a dry powder inhalable formulations. In addition to the a compound of Formula 1 or a structural analogue thereof, a sulfono-γ-AA peptide according to Formula 1 or a structural analogue thereof, a sulfono-γ-AA peptide according to Formula 1 or a structural analogue thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets.

The parenteral formulations can be administered to a subject in need thereof. The parenteral formulations can be administered to a subject in need thereof, a population of cells, and/or a population of cells in a subject in need thereof. In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

For some embodiments, the dosage form contains a predetermined amount of a compound of Formula 1 or a structural analogue thereof, a sulfono-γ-AA peptide according to Formula 1 or a structural analogue thereof, a sulfono-γ-AA peptide according to Formula 1 or a structural analogue thereof, auxiliary active ingredient, and/or pharmaceutically acceptable salt thereof per unit dose. In an embodiment, the predetermined amount of the compound of Formula 1 or a structural analogue thereof, a sulfono-γ-AA peptide according to Formula 1 or a structural analogue thereof, a sulfono-γ-AA peptide according to Formula 1 or a structural analogue thereof, auxiliary active ingredient, and/or pharmaceutically acceptable salt thereof can be an effective amount, a least effect amount, and/or a pharmaceutically effective amount. In some aspects, the predetermined amount can be effective, to improve working memory in a subject in need thereof. In some aspects, the predetermined amount can improve cellular viability in a population of cells or population of cells in a subject. In some aspects, the predetermined amount can be effective to treat, prevent, or mitigate the symptoms of a neurodegenerative disease in a subject having or suspected of having a neurodegenerative disease, for example Alzheimer's disease, Parkinson's disease, Huntington's disease, amyotrophic lateral sclerosis (ALS), other acute or chronic neuronal damage, spinal cord damage, and trauma brain injury.

In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Sulfono-γ-AA Peptides

The compounds and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Using the Pharmaceutical Formulations

Any amount pharmaceutical formulations described herein can be administered to a subject in need thereof one or more times per day, week, month, or year. In some embodiments, the pharmaceutical formulation administered contains an effective amount, a least effective amount, and/or a pharmaceutically effective amount of the compound of Formula 1 or a structural analogue thereof, a a sulfono-γ-AA peptide according to Formula 1 or a structural analogue thereof, and/or a sulfono-γ-AA peptide according to Formula 1 or a structural analogue thereof. For example, the pharmaceutical formulations can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year. a neurodegenerative disease.

In some embodiments, the subject in need thereof to which the pharmaceutical formulation is administered to can have a disease or disorder in which working memory is impaired, or another condition in which the subject is experiencing working memory loss. Such a disease or disorder can be a nervous system disease or disorder, for example, Alzheimer's disease, Parkinson's disease, Huntington's disease, amyotrophic lateral sclerosis (ALS), other acute or chronic neuronal damage, spinal cord damage, and trauma brain injury. The subject in need thereof can be a subject experiencing symptoms of Alzheimer's disease (such as working memory loss) or otherwise suspected of having Alzheimer's disease. Assays to assess working memory loss in subjects are known in the art.

In some aspects, the subject can have a disease or disorder in which cellular viability is negatively affected compared to a non-diseased control. In particular, populations of cells whose viability can be affected include neuronal cells and spleen cells. In certain aspects, the subject or subject in need thereof can also be a population of cells whose viability is less than normal compared to a healthy population. Such population of cells can include neuronal cells or spleen cells. Suitable assays for determining if cellular viability include, but are not limited to, MTT, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have, or otherwise be suspected of having, a neurodegenerative disease or a symptom thereof (for example Alzheimer's disease, Lewy body dementia, dementia, Parkinson's disease, Huntington's disease, amyotrophic lateral sclerosis (ALS), other acute or chronic neuronal damage, spinal cord damage, and trauma brain injury and the like).

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of pharmaceutical formulations described herein can be administered in an amount ranging from about 0.01 mg to about 1000 mg per day, as calculated as the free or unsalted compound having a structure according to Formula 1 or structural analogue thereof. The amount can also be a concentration of about 0.1 μM to about 50 μM or about 0.1 μM to about 200 μM. In other embodiments, an amount delivered to a subject can be a concentration of about 5 mM/subject per day.

The pharmaceutical formulations provided herein can be administered in combinations with or include one or more other auxiliary agents. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits

The pharmaceutical formulations provided herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions can provide directions for administering the compounds, pharmaceutical formulations, or salts thereof to a subject in need thereof. In some aspects, the instructions can provide directions for administering the compounds, pharmaceutical formulations, or salts thereof to a subject having a disease or disorder in which working memory is impaired. In some aspects, the instructions can provide directions for administering the compounds, pharmaceutical formulations, or salts thereof to a subject having a disease or disorder in which cell viability (for example neuronal or spleen) is impaired. Suitable assays to assay working memory and cellular viability are known in the art. Other suitable assays will be appreciated by those of ordinary skill in the art. the instructions can provide directions for administering the compounds, pharmaceutical formulations, or salts thereof to a subject having a disease or disorder of the nervous system.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

The cell toxicity of 125-6b on N2a/APP (a human APPs we stable transfected mouse neuroblastoma cell line) and mouse primary neuron as well mouse splenocytes. The method to test the cytotoxicity is MTT assay.

Figure 1B:
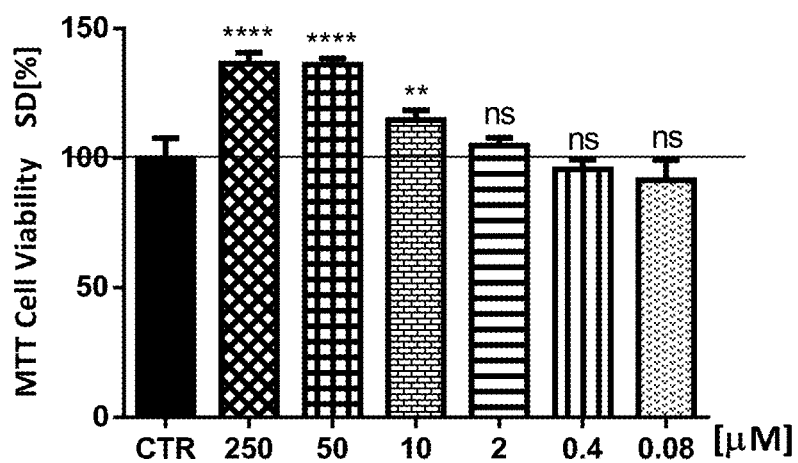

FIGS. 1A-1B are graphs showing cell viability results of a stable mouse N2a/APP cell line (transfected to stably express human amyloid precursor protein, APP) exposed to sulfono-γ-AA peptide FS-125-6-b as determined by 3-(4,5-dimethylthiazol-2-yl)-2,5-diphenyltetrazolium bromide (MTT) assay. No toxicity is observed up to 200 μM sulfono-γ-AA peptide FS-125-6-b.

Figure 2:
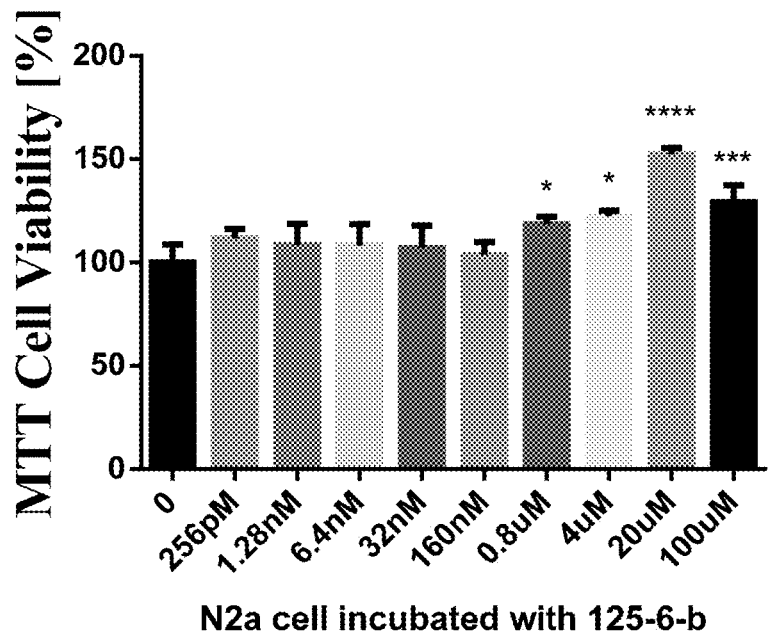
FIG. 2 is a graph showing cell viability results of a stable mouse N2a/APP cell line (transfected to stably express human amyloid precursor protein, APP) exposed to sulfono-γ-AA peptide FS-125-6-b as determined by 3-(4,5-dimethylthiazol-2-yl)-2,5-diphenyltetrazolium bromide (MTT) assay.

FIG. 2 is a graph showing cell viability results of a stable mouse N2a/APP cell line (transfected to stably express human amyloid precursor protein, APP) exposed to sulfono-γ-AA peptide FS-125-6-b as determined by 3-(4,5-dimethylthiazol-2-yl)-2,5-diphenyltetrazolium bromide (MTT) assay. No toxicity is observed, and an increase in cell viability is shown with 0.8 μM-100 μM sulfono-γ-AA peptide FS-125-6-b.

Figure 3:
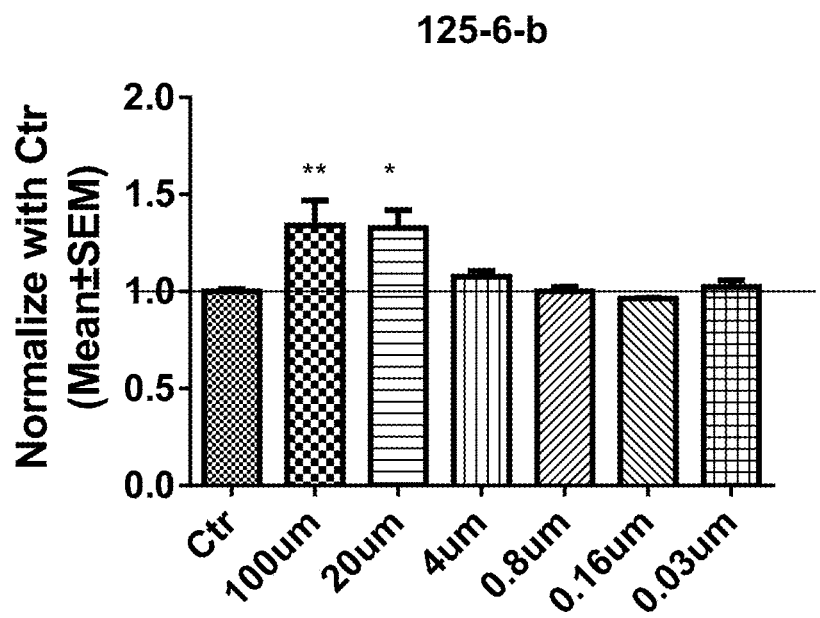
FIG. 3 is a graph showing cell viability results of murine primary neurons (derived from embryos) exposed to sulfono-γ-AA peptide FS-125-6-b as determined by 3-(4,5-dimethylthiazol-2-yl)-2,5-diphenyltetrazolium bromide (MTT) assay (and normalized to control).

FIG. 3 is a graph showing cell viability results of murine primary neurons (derived from embryos) exposed to sulfono-γ-AA peptide FS-125-6-b as determined by 3-(4,5-dimethylthiazol-2-yl)-2,5-diphenyltetrazolium bromide (MTT) assay (and normalized to control). FS-125-6b can enhance cell viability at 20-100 μM.

Figure 4A:
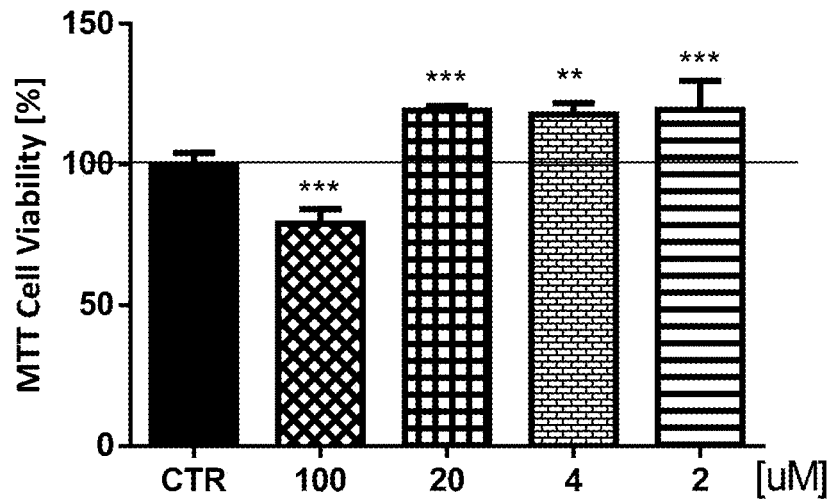
FIGS. 4A-4B are graphs showing cell viability results of murine spleen cells exposed to sulfono-γ-AA peptide FS-125-6-b as determined by 3-(4,5-dimethylthiazol-2-yl)-2,5-diphenyltetrazolium bromide (MTT) assay.
Figure 4B:
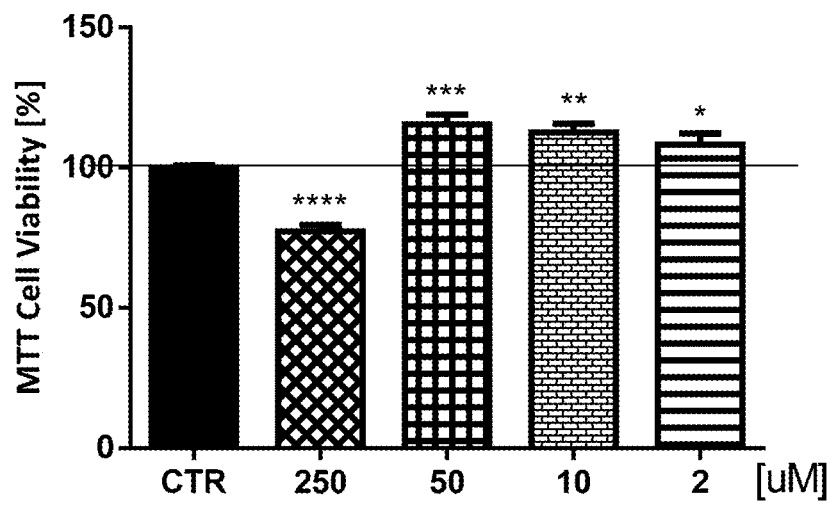

FIGS. 4A-4B are graphs showing cell viability results of murine spleen cells exposed to sulfono-γ-AA peptide FS-125-6-b as determined by 3-(4,5-dimethylthiazol-2-yl)-2,5-diphenyltetrazolium bromide (MTT) assay. FS-125-6b can enhance cell viability at 2-20 μM.

Figure 5A:
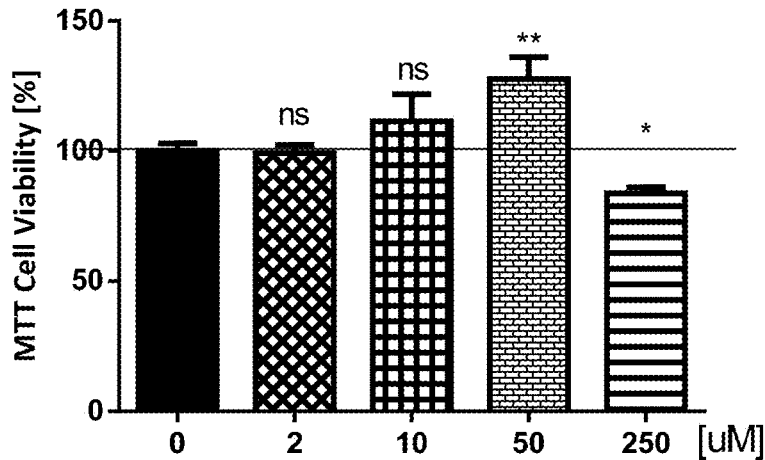
FIGS. 5A-5B are graphs showing cell viability results of murine primary neurons exposed to sulfono-γ-AA peptide FS-125-6-b as determined by 3-(4,5-dimethylthiazol-2-yl)-2,5-diphenyltetrazolium bromide (MTT) assay. Two FS-125-6-b compounds were tested: FS-1 (FIG. 5A) and FS-2 (FIG. 5B).
Figure 5B:
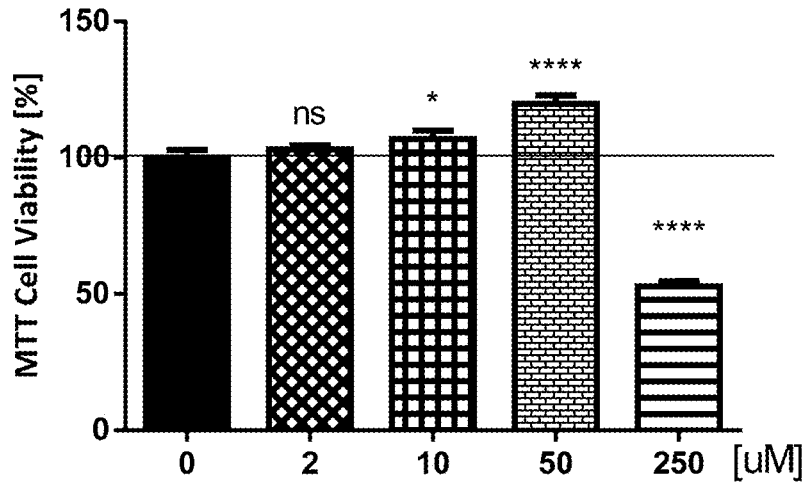

FIGS. 5A-5B are graphs showing cell viability results of murine primary neurons exposed to sulfono-γ-AA peptide FS-125-6-b as determined by 3-(4,5-dimethylthiazol-2-yl)-2,5-diphenyltetrazolium bromide (MTT) assay. Two FS-125-6-b compounds were tested: FS-1 (FIG. 5A) and FS-2 (FIG. 5B). FS-1 is the old compound and FS-2 is the new synthesis compound. They are consistent to each other but not consistent with previous results. Previous results only shows promoting growth effect on spleen cell and didn't shows promoting growth effect on primary neuron. Further FS-125-6b formulations also have no toxicity to neurons, but can enhance neuron viability as measured by MTT at 10-50 uM in primary neuron, and 10-200 uM in N2a/APP cell.

Figures 6A, 6B, 6C:
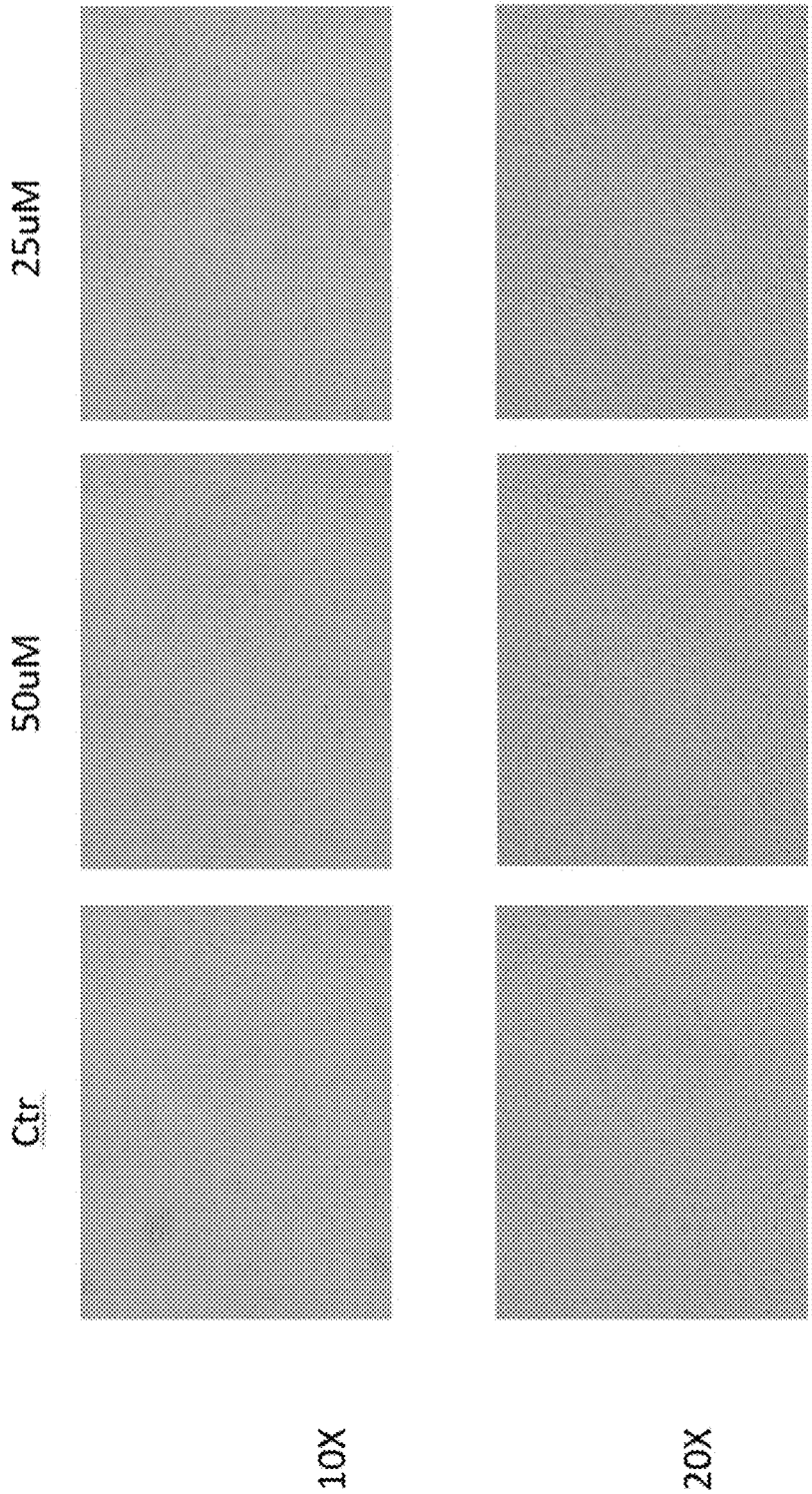
FIGS. 6A-6C are bright field micrographs showing murine primary neurons exposed to sulfono-γ-AA peptide FS-125-6-b before MTT treatment. Control cells with vehicle are shown at 10× and 20× (FIG. 6A), whereas cells exposed to sulfono-γ-AA peptide FS-125-6-b are shown at 10× and 20× in FIGS. 6B and 6C (50 μM and 25 μM, respectively).
Figures 8A, 8B, 8C:
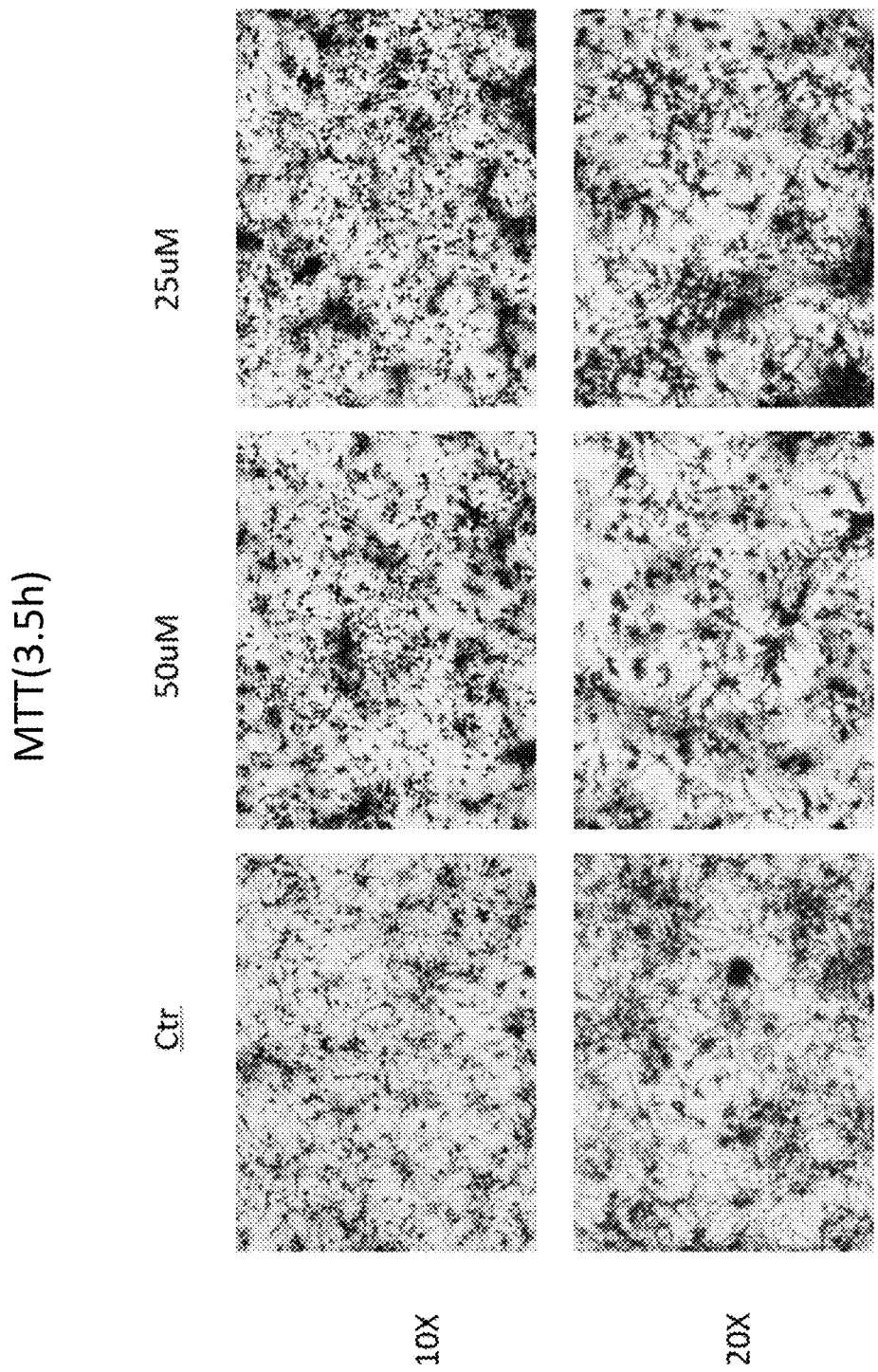
FIGS. 8A-8C are phase-contrast micrographs showing murine primary neurons exposed to sulfono-γ-AA peptide FS-125-6-b 3.5 hours into MTT treatment. Control cells with vehicle are shown at 10× and 20× (FIG. 8A), whereas cells exposed to sulfono-γ-AA peptide FS-125-6-b are shown at 10× and 20× in FIGS. 8B and 8C (50 μM and 25 μM, respectively).

FIGS. 6A-6C are bright field micrographs showing murine primary neurons exposed to sulfono-γ-AA peptide FS-125-6-b before MTT treatment. Control cells with vehicle are shown at 10× and 20× (FIG. 6A), whereas cells exposed to sulfono-γ-AA peptide FS-125-6-b are shown at 10× and 20× in FIGS. 6B and 6C (50 μM and 25 μM, respectively). FIGS. 7A-7C are bright field micrographs showing murine primary neurons exposed to sulfono-γ-AA peptide FS-125-6-b 3.5 hours into MTT treatment. Control cells with vehicle are shown at 10× and 20× (FIG. 7A), whereas cells exposed to sulfono-γ-AA peptide FS-125-6-b are shown at 10× and 20× in FIGS. 7B and 7C (50 μM and 25 μM, respectively). FIGS. 8A-8C are phase-contrast micrographs showing murine primary neurons exposed to sulfono-γ-AA peptide FS-125-6-b 3.5 hours into MTT treatment. Control cells with vehicle are shown at 10× and 20× (FIG. 8A), whereas cells exposed to sulfono-γ-AA peptide FS-125-6-b are shown at 10× and 20× in FIGS. 8B and 8C (50 μM and 25 μM, respectively).

The images of FIGS. 6A-8C are from primary neurons plated in 6-well plates. Ctr is without drug (vehicle only), whereas the treatment groups are with FS-125-6-b in DMSO (25 μM or 50 μM).

Example 2

The effect of sulfono-γ-AA peptide FS-125-6-b administration was examined in vivo in control and App/ps1 mice. APP/PS1 TG mice are double transgenic mice expressing a chimeric mouse/human amyloid precursor protein (Mo/HuAPP695swe) and a mutant human presenilin 1 (PS1-dE9), both directed to CNS neurons (Jackson Labs). Both mutations are associated with early-onset Alzheimer's disease. Working memory in animals was assessed by examining number of errors and latency in a 2-block and 3-block radial arm water maze (RAWM) behavioral test.

15 month-old mice were treated by FS-125-6-b administration at a dosage of 5 mM/mouse/day for 2 months. A breakdown of the animals used for the present study is presented in Table 1 below:

TABLE 1

Breakdown of animals use for experiments.

|  | total | Genotype | | Gender | |
|---|---|---|---|---|---|
|  |  | Ntg | PS | Male | Female |
| Ntg Ctr | 10 | 5 | 5 | 6 | 4 |
| Ntg treatment | 11 | 5 | 6 | 6 | 5 |

|  |  | APP | APP + PS1 | Male | Female |
|---|---|---|---|---|---|
| Tg Ctr | 9 | 4 | 5 | 5 | 4 |
| Tg treatment | 9 | 5 | 4 | 5 | 4 |

Behavioral Test Results

Figure 9A:
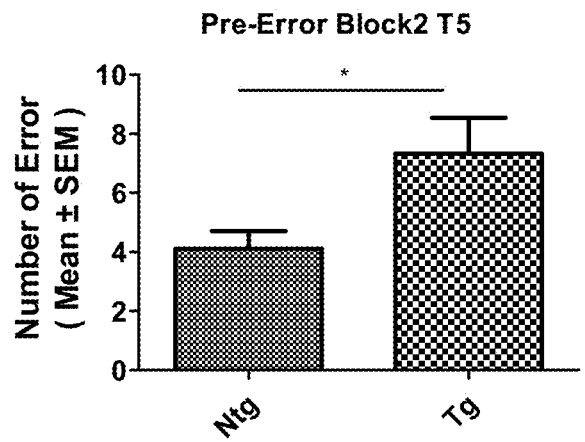
FIGS. 9A-9D are plots showing baseline behavioral data of the animals used in the present study prior to FS-125-6-b administration. NTG mice are non-transgenic mice, whereas TG mice are App/ps1 transgenic mice with the same genetic background as the NTG mice, however, overexpressing proteins associated with Alzheimer's disease. Errors (FIGS. 9A, 9C) and latency (FIG. 9B, 9D) were observed. Errors and latency were further observed at trial 1 and trial 5 (FIGS. 9C and 9D respectively).
Figure 9B:
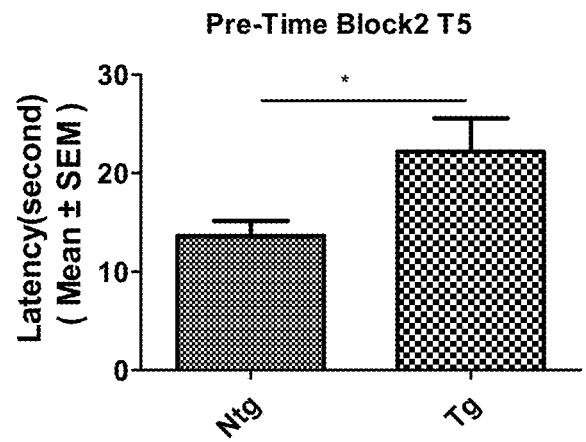
Figure 9C:
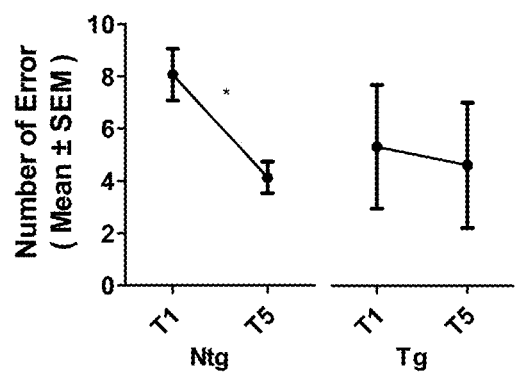
Figure 9D:
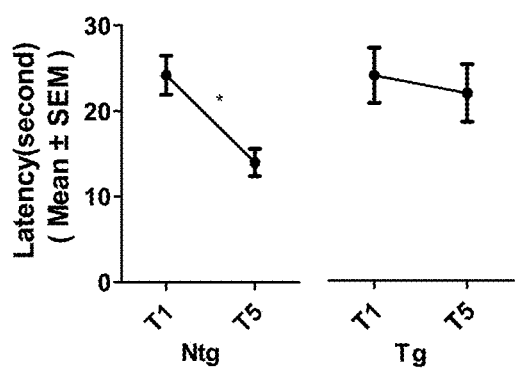
Figure 10A:
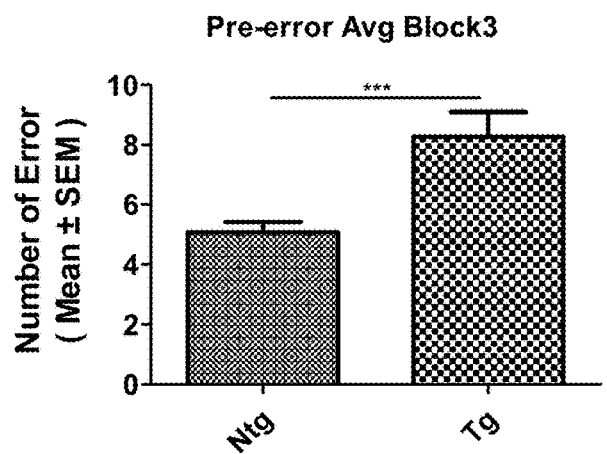
FIGS. 10A-10F are additional baseline plots showing error and latency broken down by trial average (FIGS. 10A, 10O), trial 1 (FIGS. 10B, 10D), and trial 5 (FIGS. 10E, 10F).
Figure 10B:
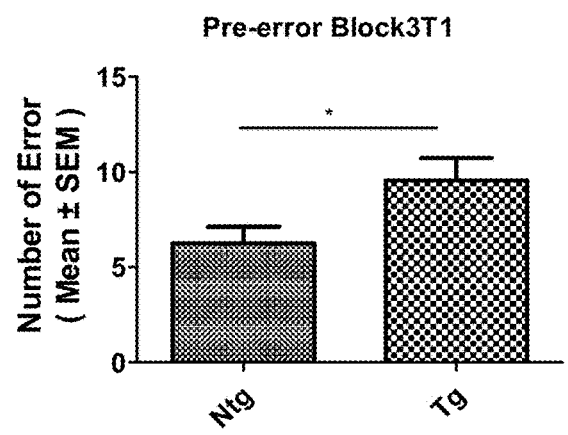
Figure 10C:
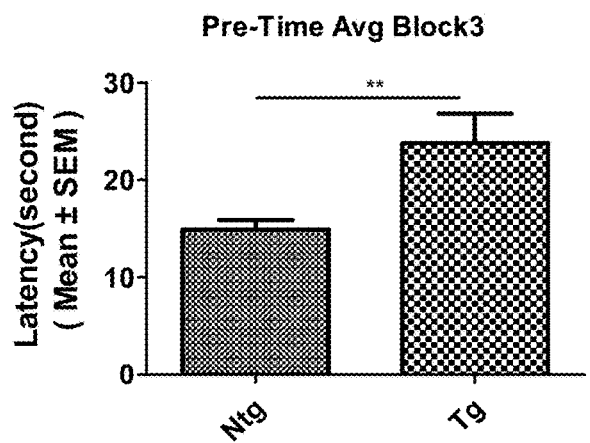
Figure 10D:
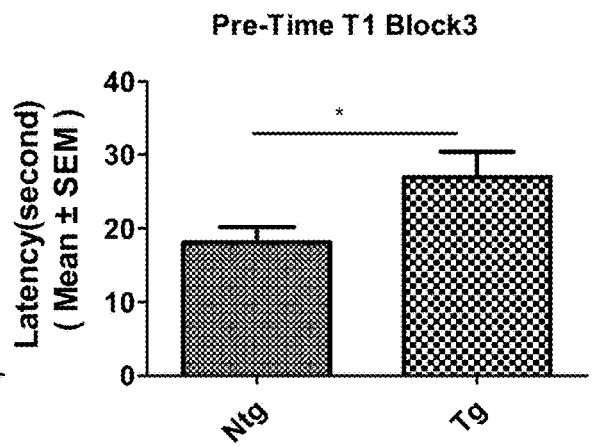
Figure 10E:
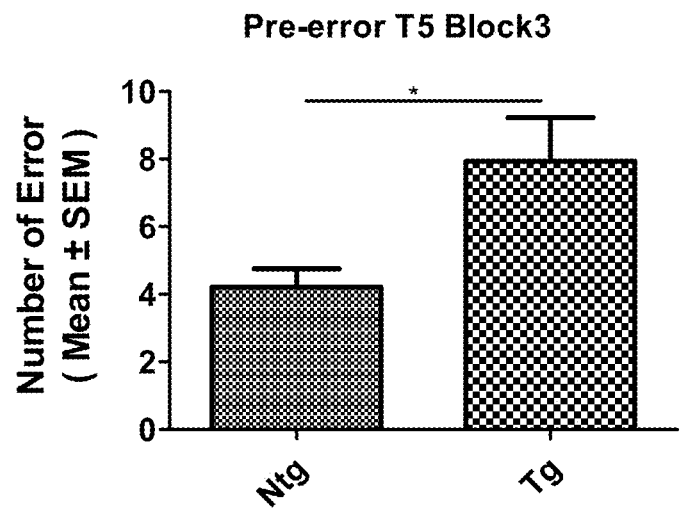
Figure 10F:
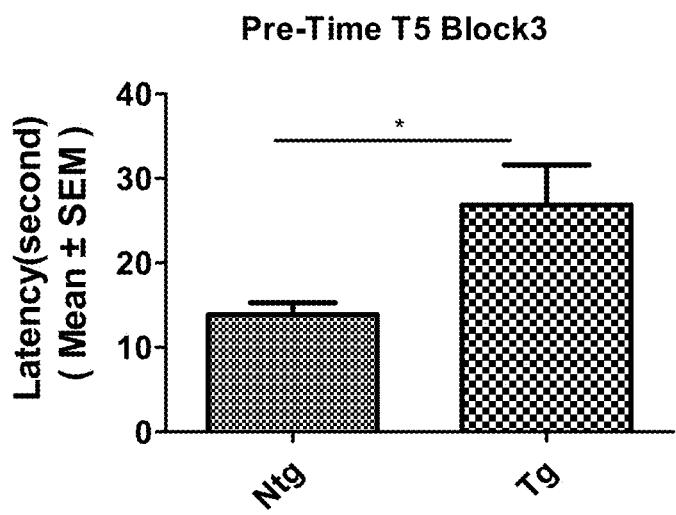

FIGS. 9A-9D are plots showing baseline behavioral data of the animals used in the present study prior to FS-125-6-b administration. NTG mice are non-transgenic mice, whereas TG mice are App/ps1 transgenic mice with the same genetic background as the NTG mice, however, overexpressing proteins associated with Alzheimer's disease. Errors (FIGS. 9A, 9C) and latency (FIG. 9B, 9D) were observed. Errors and latency were further observed at trial 1 and trial 5 (FIGS. 9C and 9D respectively). FIGS. 10A-10F are additional baseline plots showing error and latency broken down by trial average (FIGS. 10A, 10C), trial 1 (FIGS. 10B, 10D), and trial 5 (FIGS. 10E, 10F). As expected, TG mice exhibit a statistically significant increase in latency and number of errors in the tests compared with non-transgenic mice.

Figure 11A:
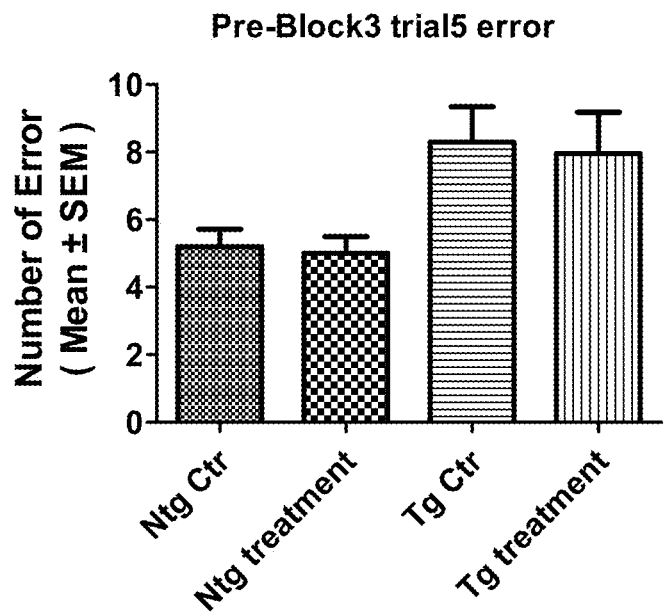
FIGS. 11A-11B are plots showing number of errors (FIG. 11A) and pre-amyloid beta 42 concentration (FIG. 11B) in animals pre- and post-treatment.
Figure 11B:
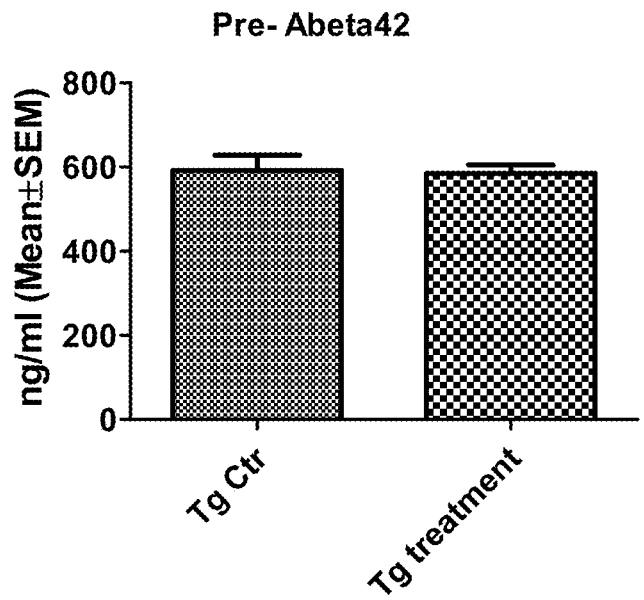

FIGS. 11A-11B are plots showing number of errors (FIG. 11A) and pre-amyloid beta 42 concentration (FIG. 11B) in animals pre- and post-treatment. A slight reduction in number of errors and pre-amyloid beta protein 42 is observed in the transgenic animals following treatment with FS-125-6-b.

FIGS. 12A-12C are plots showing Block2 number of errors (FIGS. 12A, 12C) and latency (FIG. 12B) in animals following two months of treatment with FS-125-6-b. Block 2 Trial 5 (FIGS. 12A-12B): Tg Ctr make statistically significant higher error (*P<0.5) than other groups. No statistically significant showing on latency between groups was found, although a reduction in latency in the transgenic treatment group was observed compared to the non-treated group. FIG. 12C examines trial 1 vs trial 5 (Block2). Working memory on T1 versus T5 only shows statistically significant reduction on Tg 125-6-b group (*P<0.5).

Figure 13A:
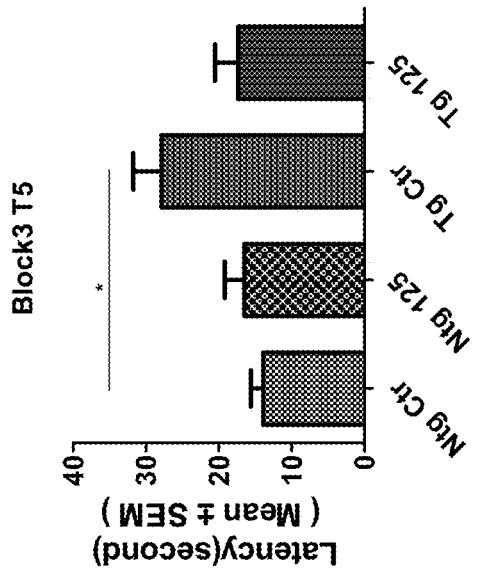
FIGS. 13A-13C are plots showing Block3 number of errors (FIGS. 13A, 13C) and latency (FIG. 13B) in animals following two months of treatment with FS-125-6-b.
Figure 13B:
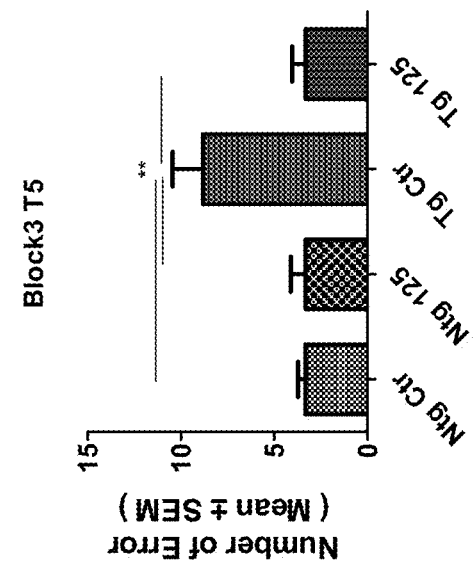
Figure 13C:
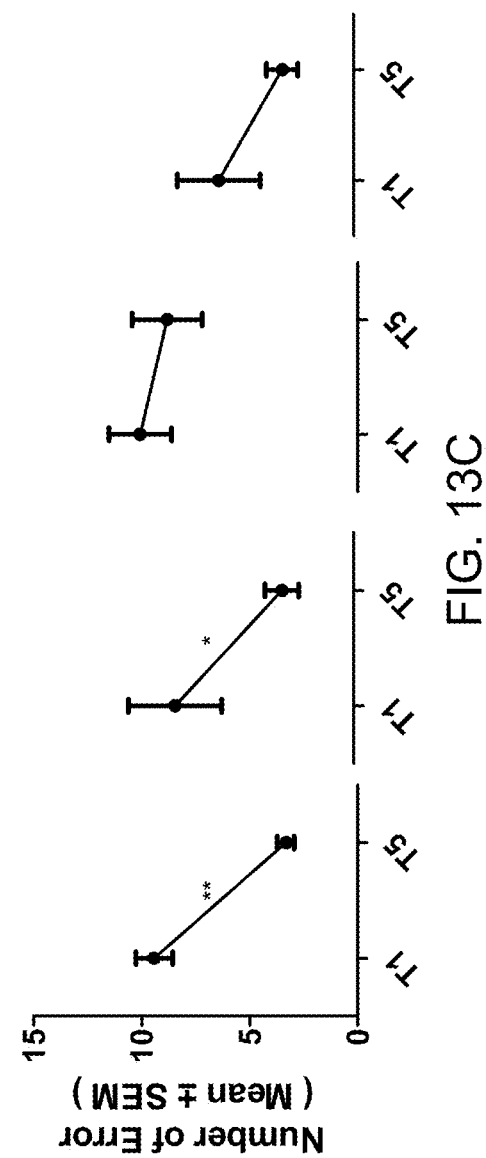

FIGS. 13A-13C are plots showing Block3 number of errors (FIGS. 13A, 13C) and latency (FIG. 13B) in animals following two months of treatment with FS-125-6-b. RAWM test results: 15 Months App/ps1 mice treated by 125-6-b 5 mM/mouse/day for 2 months (Ntg Ctr, N=7; Ntg 125-6-b, N=7; Tg Ctr, N=4; Tg 125-6-b, N=5). Block 3 Trial 5 (FIGS. 13A-13B): Tg Ctr shows statistically significant higher error (**P<0.1) than other groups, and Tg Ctr shows significant higher latency when compare with other groups. FIG. 13C examines Block 3 Trial 1 versus Trail 5. Working memory on T1 versus T5 only shows statistically significant reduction on Ntg Ctr and Ntg 125-6-b group (P<0.5), although a non-statistically significant reduction is also observed in the data with the treated transgenic group.

Flow Cytometry

FIGS. 14A-14E are plots of flow cytometry results for CD3+/CD4+, CD3/CD-, and CD8+ lymphocytes (expressed as a percentage of total lymphocytes, mean+SEM; FIGS. 14A-14C, respectively) and CD+/CD4+/CD62L- and CD+/CD4+/CD62L+ (expressed as a percentage of total CD3+/CD4+; FIGS. 14D-14E, respectively) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).

Figure 15A:
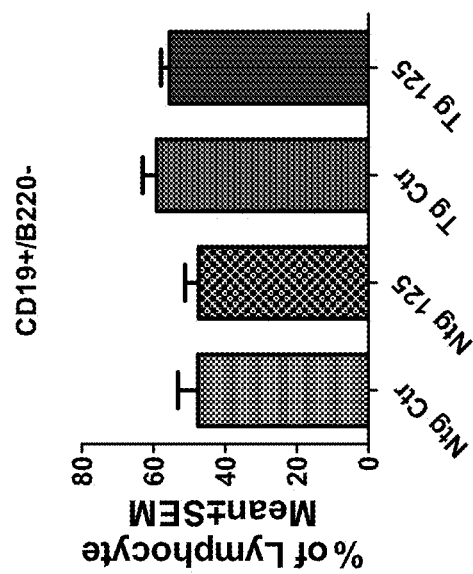
FIGS. 15A-15B are plots of flow cytometry results for CD19+/B220− (FIG. 15A) and CD19+/B220+ (FIG. 15B) lymphocytes (expressed as a percentage of total lymphocytes, mean+SEM) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).
Figure 15B:
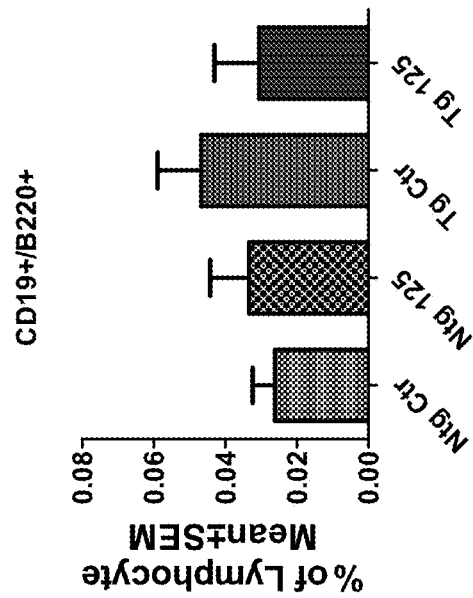

FIGS. 15A-15B are plots of flow cytometry results for CD19+/B220- (FIG. 15A) and CD19+/B220+ (FIG. 15B) lymphocytes (expressed as a percentage of total lymphocytes, mean+SEM) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).

FIGS. 16A-16D are plots of flow cytometry results for CD8a+CD11b-, CD8a+/CD11c+, CD11b+CD11c+, and CD205+/CD11b- lymphocytes (expressed as a percentage of total lymphocytes, mean+SEM; FIGS. 16A-16D, respectively) in control or FS-125-6-b treated mice (NTG and TG with two months of treatment at 5 mM/mouse/day; Ntg Ctr, N=7; Ntg 125-6-b, N=7; Tg Ctr, N=5; Tg 125-6-b, N=6).

As shown in the data at least in FIGS. 14-16, the flow data indicated that the compound has no significant impact to the immune system of the recipient subject, so it is safe from immunological perception.

We claim:

1. A sulfono-γ-AA peptide according to Formula 1 and having the structure:

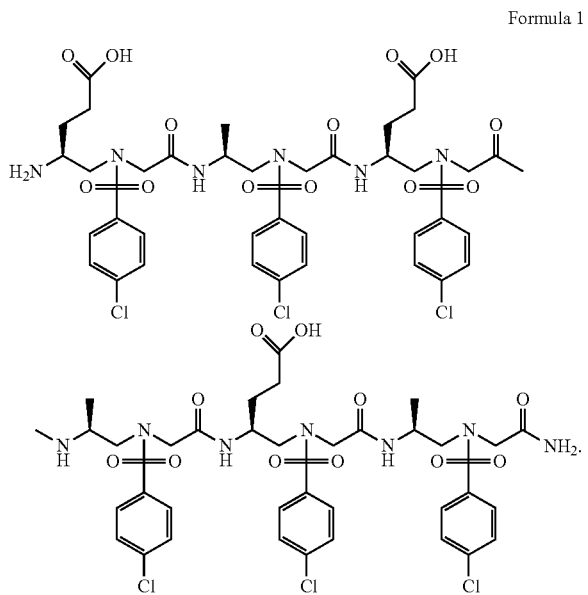

Formula 1

2. A pharmaceutical formulation comprising:
   a sulfono-γ-AA peptide according to Formula 1 and having the structure

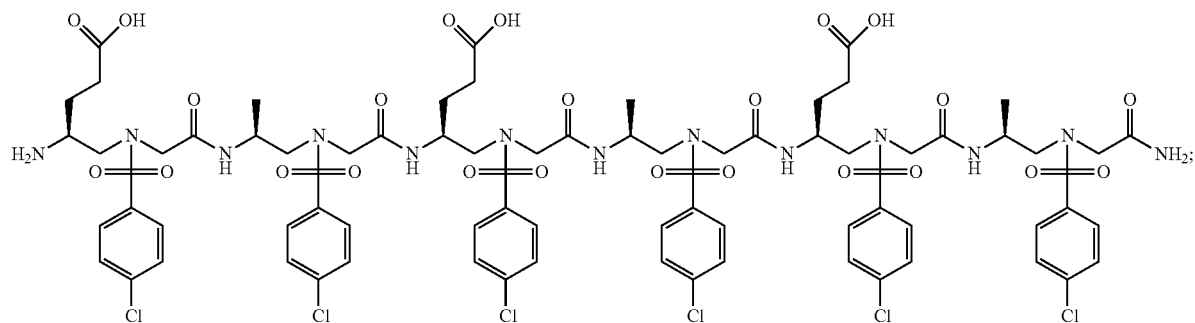

Formula 1 and
a pharmaceutically-acceptable carrier.

3. The pharmaceutical formulation of claim 2, wherein the pharmaceutical formulation comprises an effective amount of sulfono-γ-AA peptide of Formula 1.

4. The pharmaceutical formulation of claim 3, wherein the effective amount of sulfono-γ-AA peptide of Formula 1 is an amount effective to improve working memory according to a working memory assay suitable for a subject in need thereof.

5. The pharmaceutical formulation of claim 3, wherein the effective amount of sulfono-γ-AA peptide of Formula 1 is a concentration about 1 mg to 200 mg per day.

6. A method of treating Alzheimer's disease in a subject in need thereof, or a symptom thereof, the method comprising:
   administering a pharmaceutical formulation comprising a sulfono-γ-AA peptide of claim 1 to the subject in need thereof, wherein the subject in need thereof has or is suspected of having Alzheimer's disease, and wherein the sulfono-γ-AA peptide is a compound of Formula 1 and having the structure:

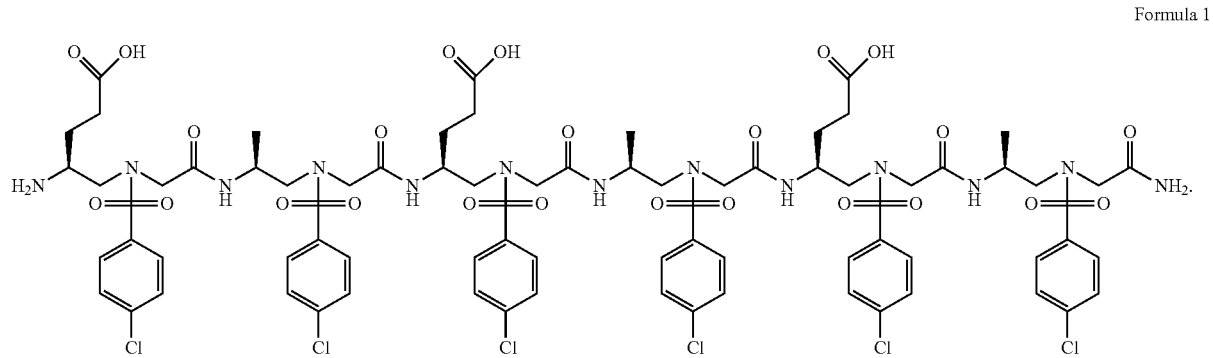

Formula 1

7. The method of claim 6, wherein the pharmaceutical formulation further comprises a pharmaceutically acceptable carrier.

8. The method of claim 6, wherein the pharmaceutical formulation comprises an effective amount of sulfono-γ-AA peptide of Formula 1.

9. The method of claim 8, wherein the effective amount of sulfono-γ-AA peptide of Formula 1 is a concentration of about 1 mg to 200 mg per day.

10. The method of claim 8, wherein the effective amount of sulfono-γ-AA peptide of Formula 1 is an amount to improve working memory in the subject in need thereof.

11. The method of claim 6, wherein the subject in need thereof performs worse in working memory tests compared to an otherwise healthy control subject as assessed by a suitable working memory assay.

12. A method of improving cellular viability in a population of spleen cells or neuronal cells from or residing in a subject having Alzheimer's disease, the method comprising:
administering a pharmaceutical formulation comprising a sulfono-γ-AA peptide of claim 1 to the spleen cells or neuronal cells from or residing in the subject having Alzheimer's disease in an amount capable of improving cellular viability in the population of spleen cells or neuronal cells.

13. The method of claim 12, wherein the pharmaceutical formulation further comprises a pharmaceutically acceptable carrier.

14. The method of claim 12, wherein the pharmaceutical formulation comprises an effective amount of sulfono-γ-AA peptide of Formula 1.

15. The method of claim 14, wherein the effective amount of sulfono-γ-AA peptide of Formula 1 is a concentration of about 1 mg to 200 mg per day.

16. The method of claim 14, wherein the effective amount of sulfono-γ-AA peptide of Formula 1 is an amount to improve cellular viability according to a MTT assay.

17. The method of claim 12, wherein the population of spleen cells or neuronal cells is from or residing in a subject having Alzheimer's disease who performs worse in working memory tests compared to an otherwise healthy control subject as assessed by a suitable working memory assay.

* * * * *